US009784656B2

(12) United States Patent
Grondin et al.

(10) Patent No.: US 9,784,656 B2
(45) Date of Patent: Oct. 10, 2017

(54) METHODS AND APPARATUS FOR MEASURING PROPERTIES OF A CANTILEVERED MEMBER

(71) Applicant: Cool Clubs, LLC, Scottsdale, AZ (US)

(72) Inventors: Simon Louis-Michel Grondin, Scottsdale, AZ (US); Mark D. Timms, Scottsdale, AZ (US)

(73) Assignee: Cool Clubs, LLC, Scottsdale, AZ (US)

( * ) Notice: Subject to any disclaimer, the term of this patent is extended or adjusted under 35 U.S.C. 154(b) by 260 days.

(21) Appl. No.: 14/643,820

(22) Filed: Mar. 10, 2015

(65) Prior Publication Data
US 2015/0253229 A1 Sep. 10, 2015

Related U.S. Application Data

(60) Provisional application No. 61/950,640, filed on Mar. 10, 2014.

(51) Int. Cl.
*G01R 31/00* (2006.01)
*G01N 3/20* (2006.01)
(Continued)

(52) U.S. Cl.
CPC .............. *G01N 3/20* (2013.01); *G01N 3/04* (2013.01); *G01N 3/068* (2013.01); *G06T 7/254* (2017.01);
(Continued)

(58) Field of Classification Search
CPC ............ G01N 3/20; G01N 3/04; G01N 3/068; G01N 3/08; G01N 3/10; G01N 2203/0023; G01N 2203/0435
(Continued)

(56) References Cited

U.S. PATENT DOCUMENTS 4,682,504 A * 7/1987 Kobayashi .......... G01M 5/0058
73/794
5,040,279 A * 8/1991 Braly ..................... A63B 53/00
29/407.07
(Continued)

FOREIGN PATENT DOCUMENTS

CN          1645401 A      7/2005
JP     CN 1645401 A   *  7/2005  ............. G06F 19/18

OTHER PUBLICATIONS

Zumbach., Bendcheck Measures the Straightness of Round—Pipes, Bars, and Rods in Real Time, Zumbach Blog, Dec. 3, 2015.*
(Continued)

*Primary Examiner* — Patrick Assouad
*Assistant Examiner* — Sean Curtis
(74) *Attorney, Agent, or Firm* — The Noblitt Group, PLLC (57) ABSTRACT

Methods and apparatus for measuring properties of a cantilevered member according to various aspects of the present technology may utilize a test stand comprising a chuck configured to secure a first end of a test member or shaft such that a second end of the test member is cantilevered outward from the chuck. A loading system may be configured to apply a force to the test member causing the test member to deflect in response to the load. An image capturing system is configured to acquire one or more images of the deflected test member and a data acquisition system may analyze the collected data and images to calculate one or more properties of the test member.

21 Claims, 8 Drawing Sheets

(51) Int. Cl.
*G01N 3/04* (2006.01)
*G01N 3/06* (2006.01)
*G06T 7/254* (2017.01)

(52) U.S. Cl.
CPC ........... *G01N 2203/0647* (2013.01); *G06T 2207/30164* (2013.01)

(58) Field of Classification Search
USPC ........ 324/750.16, 750.19; 382/107; 348/142; 356/601, 614; 72/8.3, 31.03–31.04, 72/31.07, 31.1, 293
See application file for complete search history.

(56) References Cited

U.S. PATENT DOCUMENTS

| | | | | |
|---|---|---|---|---|
| 5,309,746 A * | 5/1994 | Abbey, III | ........... | B21D 43/006 72/11.2 |
| 5,419,192 A * | 5/1995 | Maxwell | ........... | B60K 17/22 73/462 |
| 5,429,008 A * | 7/1995 | Matsumoto | ......... | G01M 5/0058 73/862.639 |
| 6,405,595 B1 * | 6/2002 | Harrison | ........... | G01L 5/00 73/573 |
| 6,526,613 B1 * | 3/2003 | Penley | ........... | A63B 60/42 73/65.03 |
| 6,532,818 B2 * | 3/2003 | Blankenship | ......... | A63B 60/42 702/43 |
| 6,571,640 B2 * | 6/2003 | Harrison | ............ | G01M 5/0058 73/65.03 |
| 6,572,488 B1 * | 6/2003 | Weiss | ........... | G01H 1/00 473/289 |
| 6,915,695 B2 * | 7/2005 | Weiss | ........... | A63B 53/00 473/289 |
| 6,968,747 B2 * | 11/2005 | Chen | ........... | G01M 1/16 473/289 |
| 6,990,865 B2 * | 1/2006 | Weiss | ........... | A63B 53/00 473/289 |
| 6,993,970 B2 * | 2/2006 | Weiss | ........... | A63B 53/00 473/289 |
| 6,997,056 B2 * | 2/2006 | Weiss | ........... | A63B 53/00 473/289 |
| 7,415,867 B2 * | 8/2008 | Spencer | ........... | A63B 53/10 33/508 |
| 7,788,982 B2 * | 9/2010 | Dee | ........... | G01N 3/04 73/760 |
| 7,808,655 B2 * | 10/2010 | Weiss | ........... | A01K 87/00 356/601 |
| 8,590,393 B2 * | 11/2013 | You | ........... | G01N 3/20 73/65.03 |
| 9,046,354 B2 * | 6/2015 | Kenner | ........... | G01B 11/24 |
| 2002/0139195 A1 * | 10/2002 | Harrison | ........... | G01M 5/0058 73/800 |
| 2003/0013541 A1 * | 1/2003 | Weiss | ........... | A63B 53/00 473/316 |
| 2005/0217379 A1 * | 10/2005 | Weiss | ........... | A63B 53/00 73/579 |
| 2005/0223802 A1 * | 10/2005 | Weiss | ........... | A63B 53/00 73/579 |
| 2010/0313672 A1 * | 12/2010 | Dee | ........... | G01N 3/04 73/851 |
| 2012/0073383 A1 * | 3/2012 | You | ........... | A63B 60/42 73/847 |
| 2012/0169869 A1 * | 7/2012 | You | ........... | A63B 53/10 348/142 |
| 2015/0253229 A1 * | 9/2015 | Grondin | ........... | G01N 3/20 382/107 |

OTHER PUBLICATIONS

Fertis et al. "Pseudolinear and Equivalent Systems for Large Deflections of Members," J. Eng. Mech. 1989.115:2440-2459.
Shiue et al., "A Study of Damping Characteristics and Shock Reduction Efficiency of Golf Shafts."

* cited by examiner

METHODS AND APPARATUS FOR MEASURING PROPERTIES OF A CANTILEVERED MEMBER

CROSS-REFERENCES TO RELATED APPLICATIONS

This application claims the benefit of U.S. Provisional Patent Application No. 61/950,640, filed Mar. 10, 2014, and incorporates the disclosure of the application by reference.

BACKGROUND OF INVENTION

Current methods of calculating and determining stiffness profiles for shafts or beams are commonly based on several assumptions based on the material and the method of bending the beam or shaft. For example, many techniques are based on the assumption that the flexural rigidity of the beam or shaft is continuous along the entire length of the beam or even sub-sections of the shaft. This, however, may not be true in many instances where the cross-sectional area or material properties of the beam are changing along its length. Some current testing methods also commonly utilize a three-point bending test that applies a load to the center of a sub-section of a beam or shaft and forms a "U-shape" deformation. This type of test is common since the associated equations can be relatively simple to solve. However, these simple equations often rely on several assumptions such as the stiffness being constant over the sub-section, deflections being largest as the center and overall deflections being small. These types of assumptions lose accuracy when deflections are large in comparison to the length of the beam and the stiffness profile and material properties are non-constant, as is the case in several beams or shafts.

SUMMARY OF THE INVENTION

Methods and apparatus for measuring properties of a cantilevered member according to various aspects of the present technology may utilize a test stand comprising a chuck configured to secure a first end of a test member or shaft such that a second end of the test member is cantilevered outward from the chuck. A loading system may be configured to apply a force to the test member causing the test member to deflect in response to the load. An image capturing system is configured to acquire one or more images of the deflected test member and a data acquisition system may analyze the collected data and images to calculate one or more properties of the test member.

BRIEF DESCRIPTION OF THE DRAWINGS

A more complete understanding of the present invention may be derived by referring to the detailed description when considered in connection with the following illustrative figures. In the following figures, like reference numbers refer to similar elements and steps throughout the figures.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various types of stands, coupling devices, image capturing devices, loading devices, measuring systems, and the like, which may carry out a variety of functions. Further, the present technology may employ any number of conventional techniques for measuring physical properties, measuring deflections in test members, applying loads to test members, and/or capturing and analyzing test data.

Methods and apparatus for measuring properties of a cantilevered member according to various aspects of the present technology may operate in conjunction with any suitable shaft and/or cantilevered member. Various representative implementations of the present technology may be applied to any system for measuring the effects of applied loads and/or identifying physical characteristics of a test member. The test member may comprise any suitable device having a longitudinal axis such as: a shaft, beam, rod, tube, column, post, rebar, and the like. The test member may also comprise a device that is swung during use such as: a golf shaft, a baseball bat, a tennis racket, a hockey stick, and the like.

Figure 1:
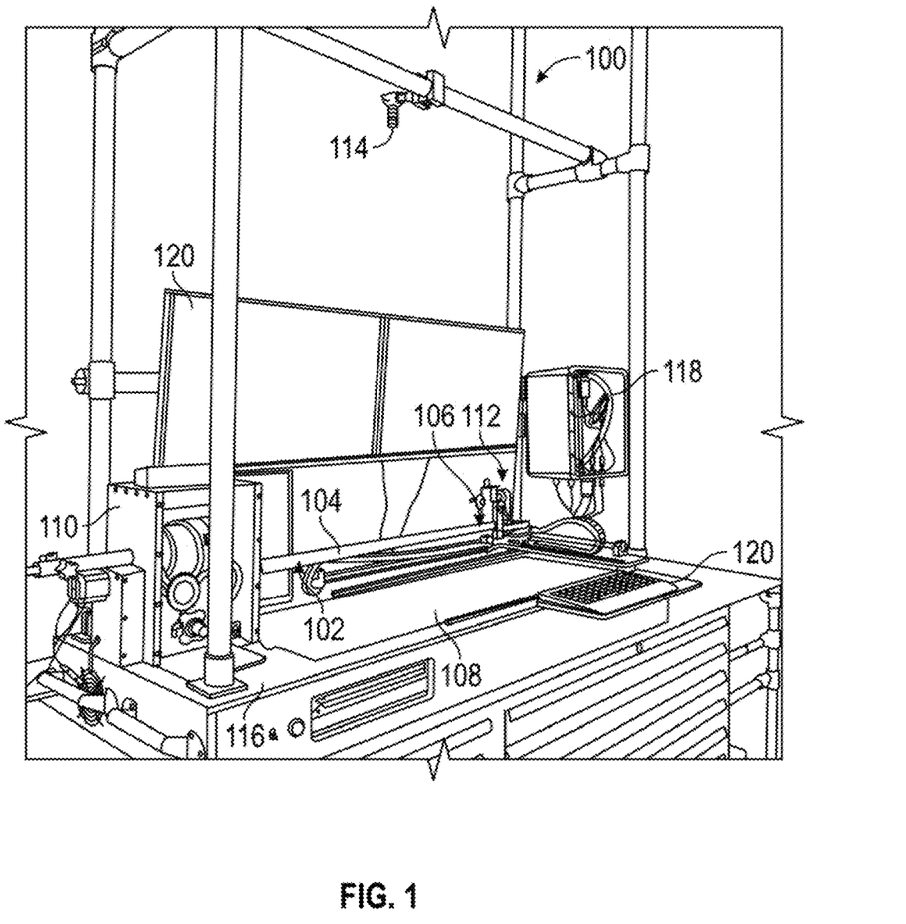
FIG. 1 representatively illustrates a test stand in accordance with an exemplary embodiment of the present technology.

Referring now to FIG. 1, in one representative embodiment, methods and apparatus for measuring properties of a cantilevered member may comprise a test stand 100 configured to receive a first end portion 102 of a shaft 104 in a chuck 110. The test stand 100 may also comprise a loading system 112 configured to transfer a bending force to a second end portion 106 of the shaft 104. When the first end portion 102 of the shaft 104 is coupled to the chuck 110, the shaft 104 may be cantilevered outward from the chuck 110 and exposed to an image capturing system comprising a light bay 108 set into a surface 116 of the test stand 100 and an image capturing device 114 set a distance from the light bay 108. A controller 118 may be communicatively linked to the loading system 112, the image capturing system and a user interface 120.

Figure 2A:
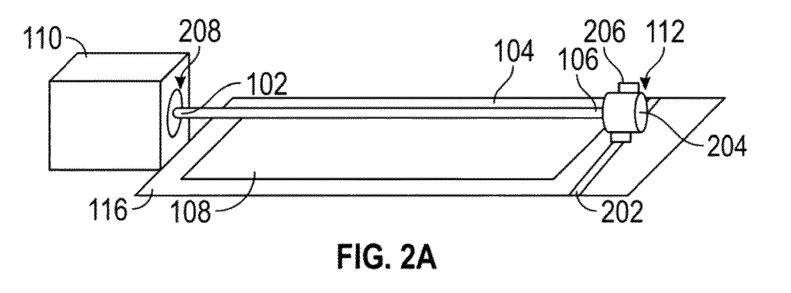
FIG. 2A representatively illustrates a perspective view of a shaft in the test stand in an unloaded position in accordance with an exemplary embodiment of the present technology.
Figure 2B:
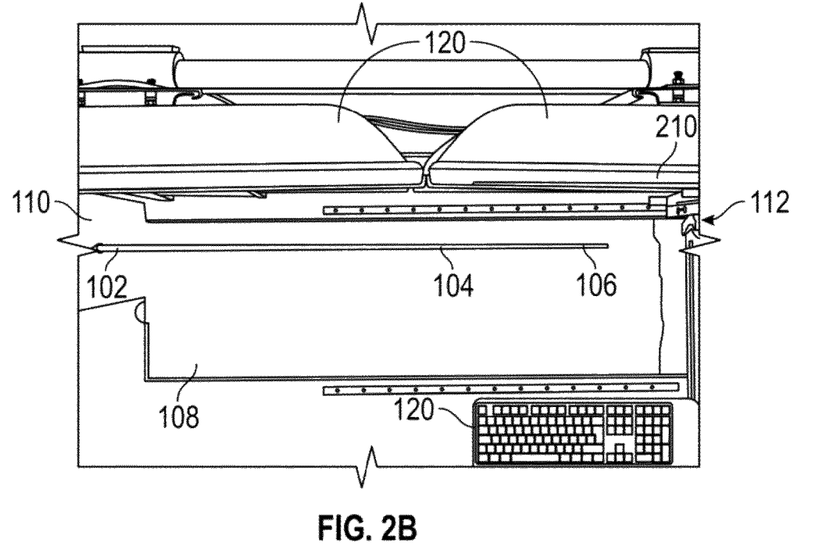
FIG. 2B representatively illustrates a top view of the shaft in FIG. 2A in an unloaded position as seen from the an image capture device in accordance with an exemplary embodiment of the present technology.
Figure 3A:
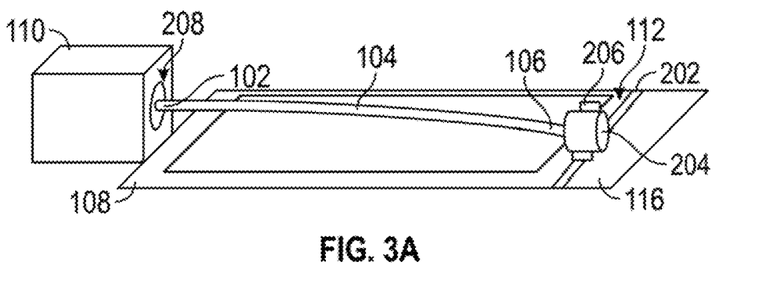
FIG. 3A representatively illustrates a perspective view of the shaft in a deflected second position in the test stand in accordance with an exemplary embodiment of the present technology.
Figure 3B:
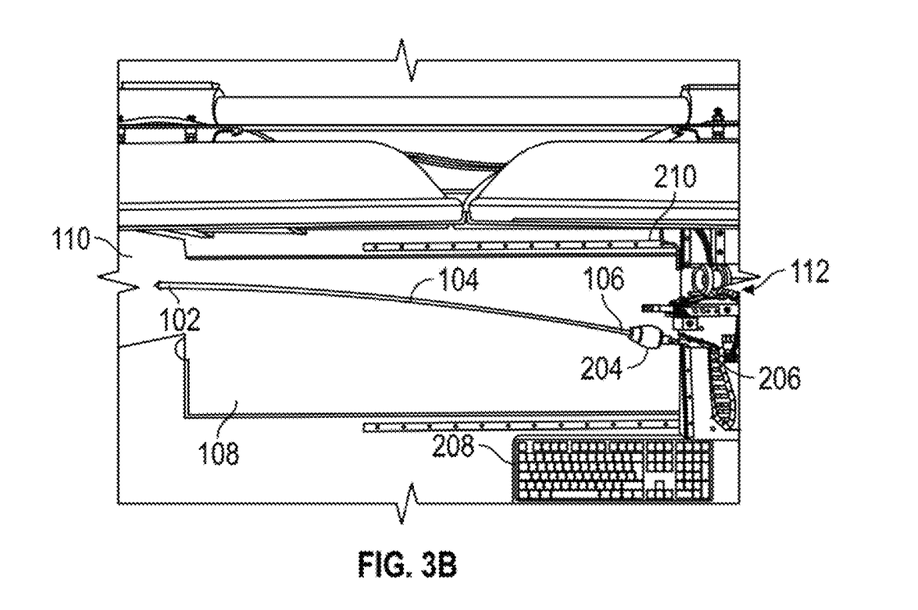
FIG. 3B representatively illustrates a top view of the shaft in FIG. 3A in a deflected second position as seen from the image capture device in accordance with an exemplary embodiment of the present technology.
Figure 4:
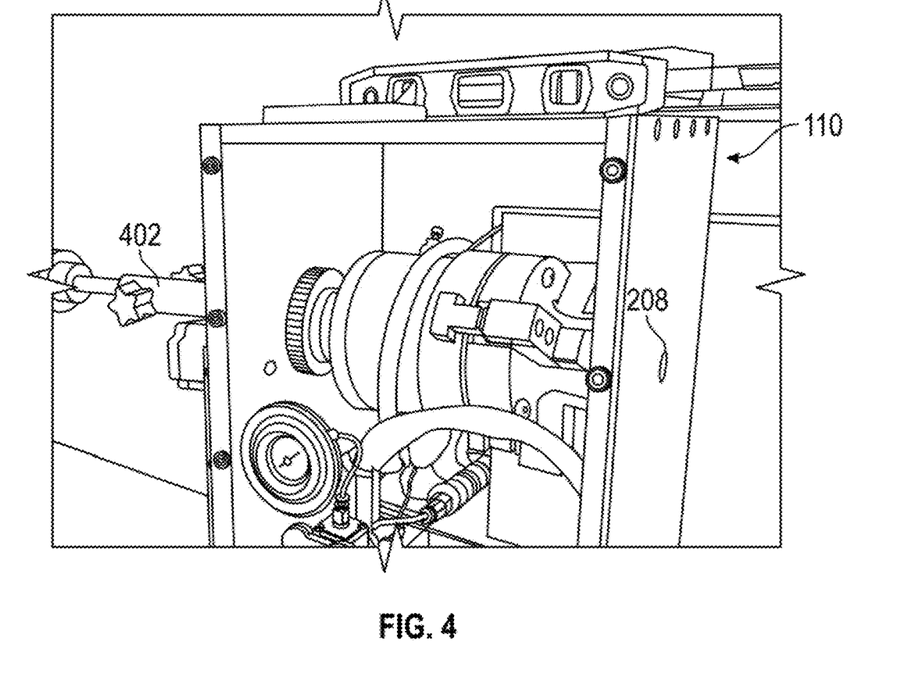
FIG. 4 representatively illustrates a perspective view of a chuck in accordance with an exemplary embodiment of the present technology.

Referring now to FIGS. 2-4, in a first embodiment, the chuck 110 secures the first end portion 102 of the shaft 104 such that the shaft 104 is held in a cantilevered manner over the light bay 108. The chuck 110 may comprise any suitable system or device for securing the shaft 104 to the test stand 100. An exterior of the chuck 110 may comprise an opening 208 suitably configured to receive a predetermined length and size of the first end portion 102 of the shaft 104. The predetermined length may comprise any suitable length and may depend at least in part on the type of shaft 104 being tested. For example, in one embodiment, between about one inch and about ten inches of the first end portion 102 of a tapered shaft 104, such as the type of shaft commonly used for a golf club, may be inserted into the opening 208 and selectively clamped to the chuck 110.

In an alternative embodiment, a total length of the shaft 104 may be more than ten feet long and require between about twelve inches and about twenty-four inches to properly cantilever the shaft 104 for testing or to simulate a desired condition. In yet another embodiment, the shaft 104 may comprise a hockey stick and may require up to about thirty-six inches to be secured by the chuck 110.

The chuck 110 may be tightened or otherwise secured to the first end portion 102 in a manner to reduce and/or prevent bending and/or displacement of the secured first end portion 102 of the shaft 104 when another portion of the shaft 104 is placed under a load. For example, the chuck 110 may comprise an adjustable butt clamp system 402 that may be secured to the first end portion 102 of the shaft 104 by an amount that substantially corresponds to the portion of the shaft 104 that may be gripped by a golfer during a golf swing.

The chuck 110 may also be configured to rotate around a longitudinal axis such that the shaft 104 may be rotated about its axis. In one embodiment, the chuck 110 may be motorized and be suitably configured to controllably rotate the shaft 104 in any desired rotational increment to facilitate bending of the shaft 104 in any desired angle of rotation or allow for an overall straightness of the shaft 104 to be determined in any desired angle of rotation. For example, a given shaft 104 may comprise various layers of materials such as graphite, carbon fiber, fiberglass, plastic, metal, epoxy, or the like that may be arranged in various directions or thicknesses along the length of the shaft 104. As a result of the multitudes of varying ways in which the layers may be arranged, the shaft 104 may exhibit differing degrees of stiffness along both its length and along a given radial line extending outward from a longitudinal axis of the shaft 104. By allowing the shaft 104 to be rotated, multiple stiffness profiles for the shaft 104 as a whole may be acquired. For example, the shaft 104 may have a first stiffness and/or straightness profile based upon the original insertion position within the chuck 110. By rotating the shaft by any amount differing from the original position a second stiffness and/or straightness profile may be determined. By increasing the number of rotations multiple stiffness and/or straightness profiles may be calculated.

The loading system 112 is configured to apply a force to the second end portion 106 of the shaft 104. The loading system 112 may comprise any suitable system or device for applying a force or displacement at a desired position along the length of the shaft 104. For example, referring now to FIGS. 2A-3 and 5, in one embodiment, the loading system 112 may comprise a robotically controlled load cell 206 configured to move perpendicular to the shaft 104 along a load platform 202 and lengthwise along the shaft 104 along a screw drive 210. The load platform 202 and the screw drive 210 may allow the load cell 206 to be positioned at any point along the length of the shaft 104 such that the load may be applied at any predetermined location.

Figure 5:
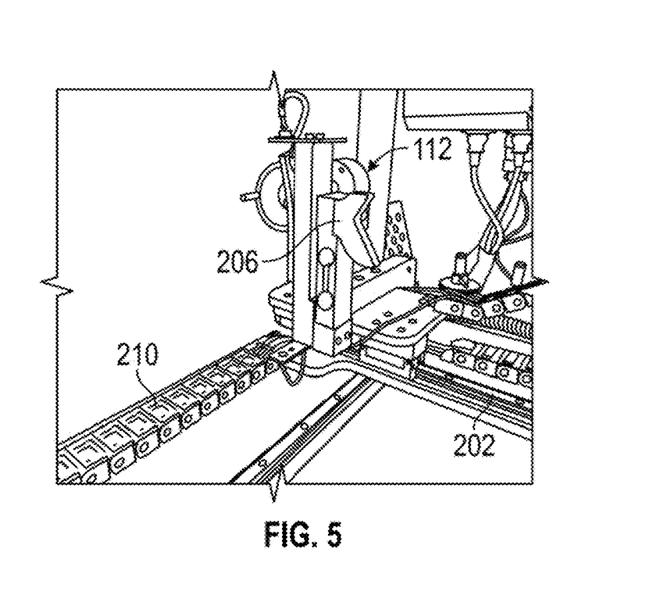
FIG. 5 representatively illustrates a perspective view of a loading system in accordance with an exemplary embodiment of the present technology.

The loading system 112 may further comprise an end effector 204 configured to be secured to the second end portion 106 and engage the load cell 206 during operation. For example, the load cell 206 may apply the desired force to the end effector 204 along a path of the load platform 202 thereby causing the shaft 104 to bend or deflect in a substantially perpendicular direction relative to the chuck 110.

The loading system 112 may be communicatively linked to or otherwise be responsive to the controller 118. For example, in one embodiment, the loading system 112 may be configured to respond to commands from the controller 118 to apply a given load or displacement to the shaft 104. The loading system 112 may further be configured to provide information such as displacement along the load platform 202, applied forces, and position along the load platform 202 or the screw drive 210 to the controller 118.

The end effector 204 is configured to be selectively coupled to the second end portion 106 of the shaft 104 to limit or otherwise prevent the second end portion 106 from being directly deflected under the effects of the applied load. The end effector 204 may be configured to be positioned over any suitable length of the second end portion 106. The length covered by the end effector 204 may be determined by any suitable criteria such as the overall length of the shaft 104, a static load on the second end portion 106, or the like.

The end effector's position and weight may also be reflective of a condition such as when a club head is attached to the second end portion 106 of a golf shaft. For example, in one embodiment, the end effector 204 may be adapted to simulate a static end load on the second end portion 106 of the shaft 104. For example, the end effector 204 may comprise a predetermined weight and be configured to be fit over a length of between about one-quarter of an inch and five inches of the second end portion 106 of the shaft 104. In this embodiment, the second end portion 106 may not itself be subjected to deflection during testing and may be reflective of a condition such as when a club head is attached to the second end portion 106 of a golf shaft. As a result, the addition of the end effector 204 to the second end portion 106 may provide a more accurate test result for the portions of the shaft 104 extending between the first and second end portions 102, 106.

Accordingly, when a force is applied to the end effector 204, deflection of the shaft 104 is limited to the section of the shaft 104 extending between the end effector 204 and the first end portion 102 that is secured by the chuck 110. In addition, the end effector 204 may help distribute the applied force over a greater length of the second end portion 106 of the shaft 104 thereby reducing any point loading at the second end portion 106 that might damage or otherwise comprise the structural integrity of the shaft 104.

The load cell 206 may comprise any system or device configured to apply a desired load to the shaft 104. In one embodiment, the load cell 206 may be configured to apply a force to the shaft 104 that is substantially perpendicular to the longitudinal axis of the shaft 104. For example, with continued reference to FIGS. 2-3B and 5, the load cell 206 may be coupled to and configured to travel along the load platform 202 to apply a load to the shaft 104 at any desired location along the length of the shaft 104. The load cell 206 may be configured to apply the load directly to the second end portion 106 or engage the end effector 204 as the load cell 206 moves along the load platform 202.

The force applied by the load cell 206 may comprise any suitable force for causing a deflection of the shaft 104. The load cell 206 may be configured, instructed, or otherwise commanded to apply a specific loading force to the second end portion 106 of the shaft 104. In one embodiment, the load cell 206 may apply a specific force load to the shaft 104 or the load cell 206 may engage and displace the shaft 104 over a specific distance and record the amount of force required to achieve the displacement. The load cell 206 may be configured to apply a force of up to about several hundred pounds in any suitable increment of force to achieve a desired amount of deflection in the shaft 104.

The amount of deflection may be determined according to any suitable criteria and may be dependent upon the type of member being tested. To provide more accurate results, a minimum amount of deflection may be required to allow the image capturing system to obtain measurable differences between the unloaded and loaded states. For example, certain types of test members such as a metal rod, stiff golf shaft, or column may not deflect sufficiently under a generic force load and instead a measurable deflection may be required to provide statistically valid results. Similarly, particularly flexible test members may deflect too much under a generic target load and statistically valid results may be better achieved by use of a target deflection.

For example, a relatively flexible golf shaft 104 may only require a force of between about two to six pounds to be applied to the end effector 204 to result in an adequate deflection of the shaft 104 to obtain a stiffness measurement. Alternatively, for a comparatively stiffer golf shaft 104, the load cell 206 may be controlled to deflect the second end portion 106 a predetermined distance of between three to seven inches. The load cell 206 or the controller 118 may then calculate the amount of force required to reach the desired deflection level. The calculated force may then be used to help determine a stiffness measurement for the shaft 104.

The load cell 206 may be configured to apply the load to the shaft 104 or end effector 204 by any suitable method. In one embodiment, the load cell 206 may be coupled to the load platform 202 which comprises a screw-drive system. The screw-drive may be configured to move the load cell 206 along a linear path that is substantially perpendicular to the axis of the shaft 104. In another embodiment, the load platform 202 may be driven along a chain or belt-drive system. In yet another embodiment, the load platform 202 may be configured to move the load cell 206 along an arc-like path to provide a substantially perpendicular force to the shaft 104 throughout the applied loading.

The load platform 202 may further be configured to measure a torque placed on the shaft 104. In one embodiment, the load platform 202 may comprise a torque sensor suitably configured to measure a torque applied to the shaft 104 by the chuck 110. The measured torque may be used to calculate a torque profile for the shaft 104.

Referring now to FIGS. 1-3B and 6, the image capturing system may be suitably configured to record the relative position of the shaft 104 during one or more stages of a testing process. The image capturing system may comprise any suitable system or device for capturing images or otherwise recording deflections along at least a portion of the length of the shaft 104. In one embodiment, the image capturing system may comprise an image capture device 114 such as a digital camera or video recorder suitably configured to capture still and/or moving images of the shaft 104. For example, the image capture device 114 may be communicatively linked to the controller 118 by any suitable methods such as via a workstation, computer terminal, test interface, or the like wherein the image capture device 114 is responsive to commands to capture images of the shaft 104 at various stages of the testing procedure including prior to, during, and after any loading has been applied by the loading system 112.

Figure 6:
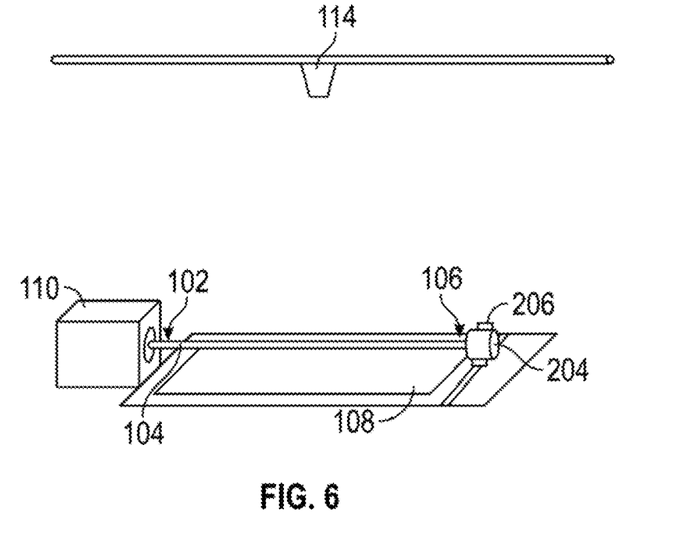
FIG. 6 representatively illustrates an image capturing system in accordance with an exemplary embodiment of the present technology.

The image capturing system may also be configured to facilitate the identification of one or more reference points that may be compared against data points collected during testing or as a basis for calibrating the test stand 100. For example, the image capture device 114 may capture images of a reference object having known properties such as a level of straightness between two end points. The resulting images may then be used as reference points or a baseline by which to compare how much a test member, such as the shaft 104, is deflected during a given test and/or how much the test member varies from the level of straightness of the reference object under no loading conditions or prior to testing.

Figure 7:
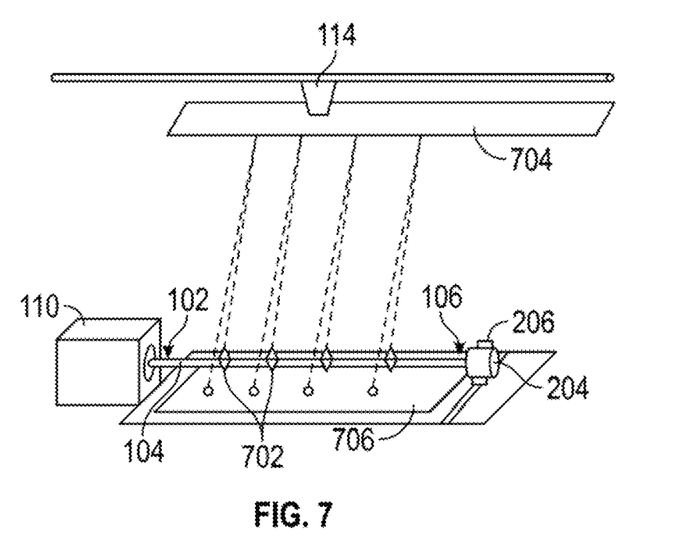
FIG. 7 representatively illustrates an alternative embodiment of an image capture system in accordance with an exemplary embodiment of the present technology.

As an alternative method of measuring deflection of the shaft 104, the image capturing system may comprise a laser line-scan machine. For example, the image capturing system 114 may comprise one or more laser line scanners configured to shine a laser upon the shaft 104 to track one or more changes in the shaft 104 under a loading condition causing a deflection and/or rotation of the shaft 104 at predetermined points along the length of the shaft 104 or along predetermined regions along the length of the shaft 104. Referring now to FIG. 7, in a second embodiment, one or more lasers may be positioned along the length of the shaft 104 itself and be configured to shine upon a surface that is suitably configured to display, capture, record, or otherwise identify any angular or longitudinal deflections experienced by the shaft 104 along pre-determined regions. For example, a series of lasers 702 may be configured to shine a laser light onto a reflective surface 704 that may redirect the laser light onto a surface 706 such as the light bay 108 that displays the individual points of light for capture by the image capture device 114. The reflective surface 704 may increase the resolution of the angular deflections of the shaft 104 by increasing the length between the laser's origin and the surface 706 on which they shine.

Referring now to FIGS. 1-3B, and 6, the light bay 108 may be configured to increase the effectiveness of the image capturing system by increasing a level of contrast between the shaft 104 and the test stand 100. The light bay 108 may comprise any suitable system or device for creating a background against which the image capture device 114 may view the shaft 104. For example, the light bay 108 may comprise a substantially flat backlit surface that is suitably configured to provide back lighting to the shaft 104. The surface of the light bay 108 may comprise any suitable material, color, or shape that may help distinguish or create contrast between the shaft 104 and any surrounding environment. By increasing the contrast of the shaft 104 relative to the background, the image capture device 114 may capture images that display the edges of the shaft 104 with greater detail to facilitate accurate edge detection of the shaft or member.

The color of the surface of the light bay 108 may be determined according to the type of test member. For example, the surface may be configured to provide a white background to the shaft 104. Alternatively, the light bay 108 may be configured to alter the color of the background to accommodate varying types of colors of test members. For example, the light bay 108 may comprise a series of light emitting diodes that may be controlled to change color to provide varying amounts of contrast between the shaft 104 and the light bay 108.

Figure 8A:
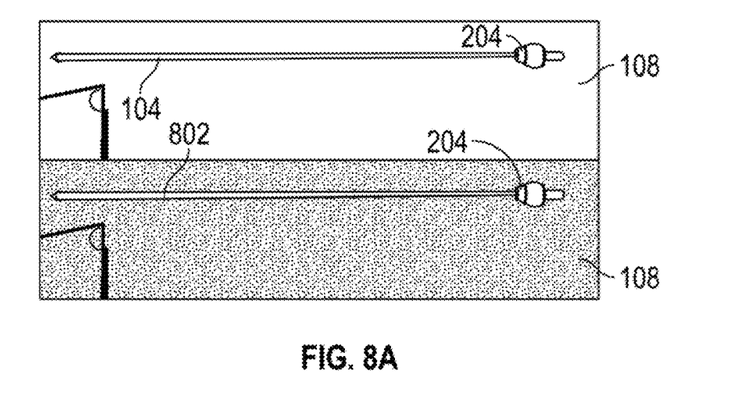
FIG. 8A representatively illustrates a conversion of an image of a shaft in an unloaded state acquired by the image capturing system in accordance with an exemplary embodiment of the present technology.
Figure 8B:
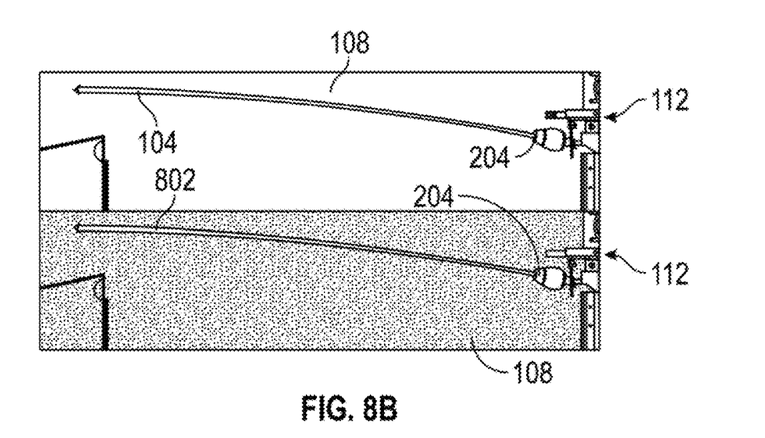
FIG. 8B representatively illustrates a conversion of an image of the shaft in a loaded state acquired by the image capturing system in accordance with an exemplary embodiment of the present technology.

The captured images may then be subject to an edge detection algorithm run by the controller 118, data acquisition system 902, or any other suitable device to further identify the edges of the shaft 104. The captured image may be converted from its native file structure to a file type that provides greater distinction of the shaft relative to its surroundings. For example, referring now to FIGS. 8A and 8B, the actual images of the shaft 104 in an unloaded state and a loaded state may be converted from a file format created by the image capture device 114 into a bitmap to produce a black and white version of the captured images. Alternatively, various properties of the captured images may be altered to increase the ability to detect the edges of the shaft 104. For example, the actual images of the shaft 104 in an unloaded state and a loaded state may be adjusted to form a negative of the original image or have the contrast settings adjusted such that the adjusted shaft image 802 is more clearly distinct against the light bay 108.

Figure 9:
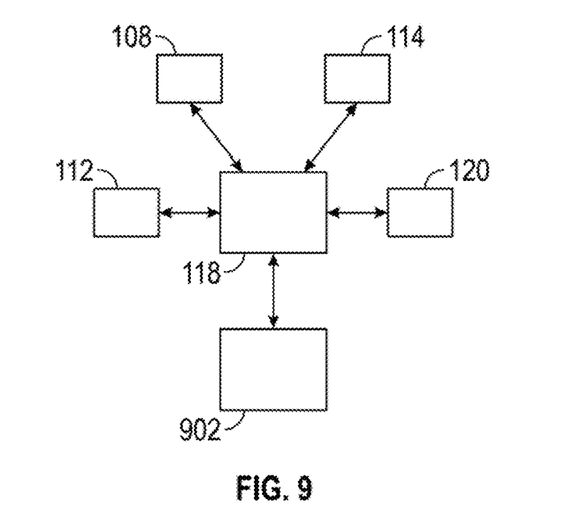
FIG. 9 represents a block diagram of various hardware components in accordance with an exemplary embodiment of the present technology FIG. 10 representatively illustrates a flow chart of a process for measuring a straightness of a shaft in accordance with an exemplary embodiment of the present technology.

Referring now to FIG. 9, the controller 118 may control and/or coordinate movement of various components of the test stand 100 such as the load cell 206, torque sensor, the load platform 202, the image capturing system, and the chuck 110. The controller 118 may comprise any suitable device or system for controlling hardware or software such as: a terminal comprising individual hardware controllers, a workstation, a personal computer terminal, a test interface, or the like. The controller 118 may also comprise one or more power supplies adapted to power, control, or regulate the various components of the test stand 100.

The controller 118 may also be responsive to input commands from the user interface 120 to initiate a testing sequence, a calibration process, or any other suitable function of the test stand 100. Accordingly, the controller 118 may be communicatively linked to the load cell 206, the load platform 202, the image capturing system, torque sensor, and the chuck 110 and be suitably configured to send and receive signals, data, instructions, and the like between each component by any suitable method such as over a wireless network or other wireless protocol, a local area network, direct data connection, and the like.

The controller 118 may also be configured to provide commands or instructions to one or more components of the test stand 100 based on data received from any individual component. For example, the controller 118 may provide a first signal to the loading system 112 to apply a force of six pounds to the end effector 204. The controller 118 may then receive a second signal from the loading system 112 confirming the instruction which causes the controller 118 to send a third signal to the image capturing system to begin capturing images of the shaft 104. The captured images may then be sent by the image capturing system directly to the controller 118 for additional processing or the captured images may be sent directly to a data acquisition system 902 for processing.

With continued reference to FIG. 9, the data acquisition system 902 may collect data from the loading system 112, the chuck, and the image capturing system for use in calculating one or more parameters of the test member such as stiffness, straightness, torsional rigidity, and dampening properties. The data acquisition system 902 may comprise any suitable system or device for processing data according to desired criteria such as a workstation, personal computer terminal, test station, or the like. The data acquisition system 902 may be integrated into the controller 118 or comprise a separate system communicatively linked to the controller 118. The data acquisition system 902 may be configured to receive, translate, convert, or otherwise process any type of data stream collected into a format that may be used to calculate the desired properties of the test member.

For example, in one embodiment, the data acquisition system 902 may comprise an analysis engine configured to compare pre-loading and post-loading images from the image capturing system to calculate a stiffness profile for the test member. The data acquisition system 902 may also be configured to compare pre-loading images against a baseline reference to calculate a straightness value/score for the test member.

The data acquisition system 902 may also be suitably configured to account for any distortions within the captured images that may be caused by the image capture device 114 itself. For example, a single camera system may have a tendency to introduce a slight bending effect to the captured image along the sides of the image due, at least in part, to the lens and a distance the camera is positioned from the shaft 104. In one embodiment, a calibration process may account for tangential and radial distortion through a standard camera calibration process that comprises taking several images of a calibration board to identify a calibration matrix that may be used to minimize distortion of the image capturing system 114.

The user interface 120 may provide operator control or access to the test stand 100. The user interface 120 may comprise any suitable device or system for allowing a user or operator to run a testing sequence, analyze results, access print, copy, or forward test results, or otherwise use the test stand 100. In one embodiment, the user interface 120 may comprise a display and an input device such as a keyboard or a mouse. In a second embodiment, the display and the input device may be combined into a single component such as a touch screen display or table computer linked to the controller 118.

Figure 10:
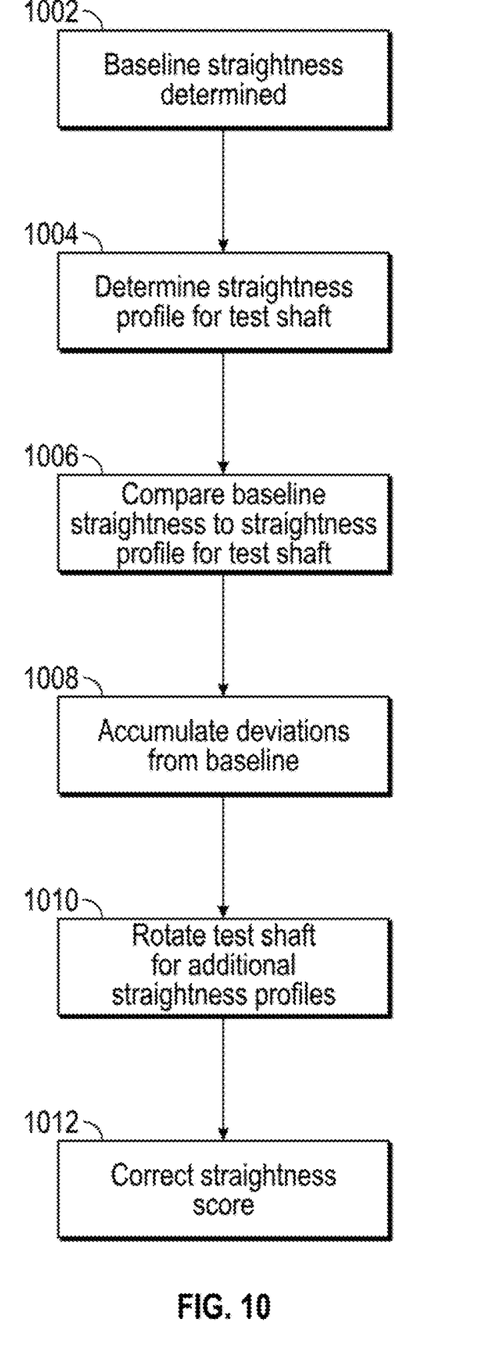
Figure 12:
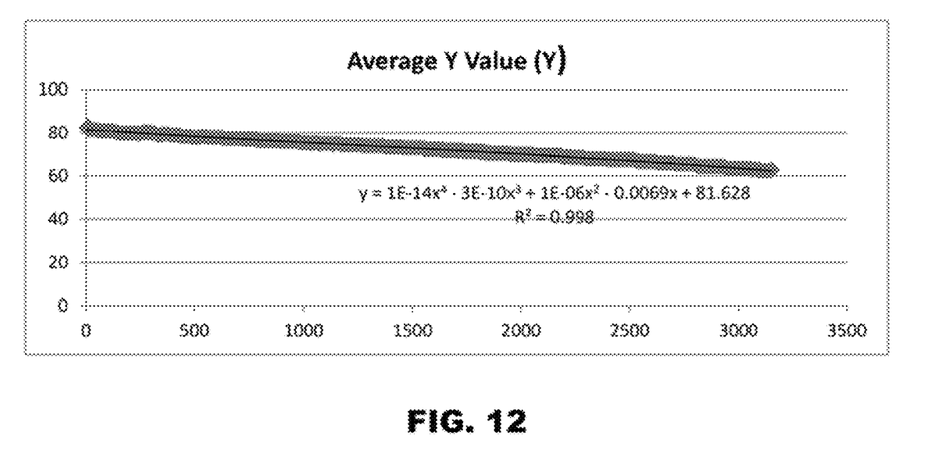
FIG. 12 representatively illustrates a plot of an average edge measurement at each pixel along the x-direction of a shaft in accordance with an exemplary embodiment of the present technology.

Referring now to FIGS. 9 and 10, the test stand 100 may also be calibrated to measure straightness. For example, a calibration rod, or reference member, having a straightness tolerance of approximately 0.005" per fool or better may be used to create a baseline straightness datum. Since the straightness of the calibration rod can be assumed to be straight relative to the members being tested, its position can be detected using the image capturing system and a datum can be established for what a zero deflection straight member would be (1002). This calibration accounts for misalignments between the image capturing system and chuck 110 which holds the first end 102 of the shaft 104, and may also account for the chuck 110 not rotating the shaft 104 truly about its axis. The test shaft 104 may then be inserted and secured to the chuck 110 and the controller 118 may then direct the chuck 110 and the image capturing system to determine a first straightness profile for the shaft 104 and store the resulting profile as reference data in the data acquisition system 902 for later use and/or calculations (1004). The first straightness profile may be determined by converting an image of the shaft 104 taken by the image capture device 114 from an image file into an alternate file type such as a bitmap. The data acquisition system 902 may then analyze the edges of the shaft 104 to determine a vertical edge position for each point of interest along the length of the shaft 104. Each point of interest may be determined according to any suitable criteria and may comprise a series of incremental steps along the length of the shaft 104 of between about one hundredth of an inch and about 5 inches For example, an upper and lower edge measurement may be taken at each pixel along the x-direction (an excerpt of data values is shown in Table 1 below). An average of the two edge measurements may be taken and plotted as shown in FIG. 12. The plotted data may be subjected to a polynomial fit to obtain a polynomial equation that may be used to calculate a revised average vertical position. This calculated value may then be compared against a value from the calibration rod at each x-location to obtain a difference of the shaft 104 from the calibration rod (1006). The difference at each x-location may then be summed for the entire length of the shaft 104 and stored as an initial straightness value for the shaft 104 (1008) for the current rotational position.

TABLE 1

| X Value (pixel) | Top Edge Y Value (pixel) | Bottom Edge Y Value (pixel) | Average Y Value (pixel) | Average Y Value of shaft based on polynomial fit (pixel) | Generated Y Values based on the Calibration Member (pixel). | Delta from Baseline (pixel) |
|---|---|---|---|---|---|---|
| 0 | 49 | 116 | 82.5 | 81.6278 | 81.7391 | 0.1113 |
| 1 | 49 | 116 | 82.5 | 81.6209 | 81.7325 | 0.1116 |
| 2 | 49 | 116 | 82.5 | 81.614 | 81.7259 | 0.1119 |
| 3 | 49 | 116 | 82.5 | 81.6072 | 81.7193 | 0.1121 |
| 4 | 50 | 116 | 83 | 81.6003 | 81.7127 | 0.1124 |
| 5 | 50 | 115 | 82.5 | 81.5934 | 81.7061 | 0.1127 |
| . | . | . | . | . | . | . |
| 100 | 55 | 107 | 81 | 80.9519 | 81.0789 | 0.127 |
| 101 | 55 | 107 | 81 | 80.9453 | 81.0723 | 0.127 |
| 102 | 55 | 107 | 81 | 80.9386 | 81.0657 | 0.1271 |
| 103 | 55 | 107 | 81 | 80.932 | 81.0591 | 0.1271 |
| 104 | 55 | 107 | 81 | 80.9254 | 81.0525 | 0.1271 |
| 105 | 55 | 107 | 81 | 80.9187 | 81.0459 | 0.1272 |
| . | . | . | . | . | . | . |
| 1000 | 54 | 97 | 75.5 | 75.6323 | 75.1367 | 0.4956 |
| 1001 | 54 | 97 | 75.5 | 75.6269 | 75.1301 | 0.4968 |
| 1002 | 54 | 97 | 75.5 | 75.6215 | 75.1235 | 0.498 |
| . | . | . | . | . | . | . |
| 2000 | 53 | 87 | 70 | 70.1544 | 68.5343 | 1.6201 |
| 2001 | 53 | 87 | 70 | 70.1486 | 68.5277 | 1.6209 |
| 2002 | 53 | 87 | 70 | 70.1428 | 68.5211 | 1.6217 |
| 2003 | 53 | 87 | 70 | 70.137 | 68.5145 | 1.6225 |
| . | . | . | . | . | . | . |
| 3000 | 49 | 78 | 63.5 | 63.5488 | 61.932 | 1.6168 |
| 3001 | 49 | 78 | 63.5 | 63.5412 | 61.9254 | 1.6158 |
| 3002 | 49 | 78 | 63.5 | 63.5335 | 61.9188 | 1.6147 |

The chuck 110 may then optionally, rotate the shaft 104 by any suitable angle of between one and 360 degrees before a second straightness value for the shaft 104 is determined to account for any two-dimensional limitations that may be inherent to or potentially be introduced by the image capturing system. The chuck 110 may continue to rotate the shaft 104 in substantially equal increments until a complete profile for the shaft 104 is determined based on an established straightness value for each rotational position of the chuck 110. For example, in one embodiment the chuck 110 may rotate the shaft 104 by increments of between fifteen and twenty-five degrees that match equal increments of rotation on the calibration rod (1010). The shaft 104 may then be compared to the baseline straightness value acquired at the same increments. Any deviations of the shaft 104 from the baseline straightness line are accumulated in an integration method to obtain a straightness score for the shaft 104. This accumulated score may be divided by the length of the shaft 104 so that a longer shaft 104 doesn't necessarily result in a worse score than a shorter shaft 104 (1012).

This method of measuring straightness may account for imperfections present in the entire length of the shaft 104 and any of its deviations from a straight line will result in a worse straightness score. This method also reduces inconsistencies that may be associated with operator-based testing such as inaccuracies resulting from the operator reading a gauge using only his/her eye.

The elements of the test stand 100 may be configured to measure the relative stiffness ("EI" or flexural rigidity) of a test member such as a rod, shaft, beam, or any other similar object. "E" represents Young's Modulus and "I" represents the second moment of inertia of a cross-section of the test member. It is known that both "E" and "I" may vary independently of each other along the length of certain types of test members such as a golf shaft 104. As a result, the test stand 100 may be configured to implement a technique of measuring the EI of a shaft 104 which calculates a continuous EI function over the length of the shaft 104 visible to the image capturing system by simulating how the shaft 104 may bend under loading such as during one or more phases of a golf swing.

This technique attempts to determine a continuous EI function by treating the golf shaft 104 as a cantilevered beam, where the secured first end portion 102 of the shaft 104 simulates the portion of the shaft 104 held by a user and the second end portion 106 simulates the portion of the shaft 104 inserted into a club head. Traditional bending equations for cantilevered beams, however, may not provide accurate test results because they are generally intended for beams that experience small deflections under loading and generally have a constant EI along the length of the beam being tested. Therefore, a more complex model is used by this technology to calculate an EI, or stiffness profile, for the shaft 104 as a whole.

This model calculates EI as a function of x along the length of the shaft 104 in association with a corresponding deflection of the shaft along a perpendicular y-direction according to the equation shown in Equation 1.

$$\frac{\frac{d^2 y}{dx^2}}{\left[1+\left(\frac{dy}{dx}\right)^2\right]^{\frac{3}{2}}} = -\frac{M(x)}{EI(x)}. \qquad \text{Equation 1}$$

where "M" is represented as a function of x along the length of the shaft 104 created by the applied load at point x along the length of the shaft 104. Therefore, for a given deflection profile for a shaft 104 represented by the deflection in the y-direction as a function of length in the x-direction, or along the shaft 104, the first and second derivatives may be determined and EI may be determined at any point along the shaft 104.

The resulting EI profile, however, may not provide the most accurate results since any empirically calculated differential may introduce noise or propagate errors. To account for this type of error, a high order polynomial is fit to the deflection profile according to the captured images of the shaft 104 when deflected by the loading system 112. The equation can then be solved at any given point along the shaft 104 and the EI profile for the shaft 104 as a whole may be calculated.

The test method obtains continuous EI data for the length of a shaft 104 and may more accurately replicates the way a shaft 104 is loaded in a golf swing. The resulting EI profile may also be more accurate because the test method/equation does not rely on simplifying assumptions associated with prior art test systems. This method also allows measurements along the total length of the shaft 104 between the first and second end portions 102, 106, unlike other methods such as a 3-point bending method that uses segmented lengths of a member. This method also reduces inconsistencies associated with operator-based testing such as those that may be introduced as a result of an operator reading a gauge using his/her eye or movement of the member by the operator during testing.

Figure 11:
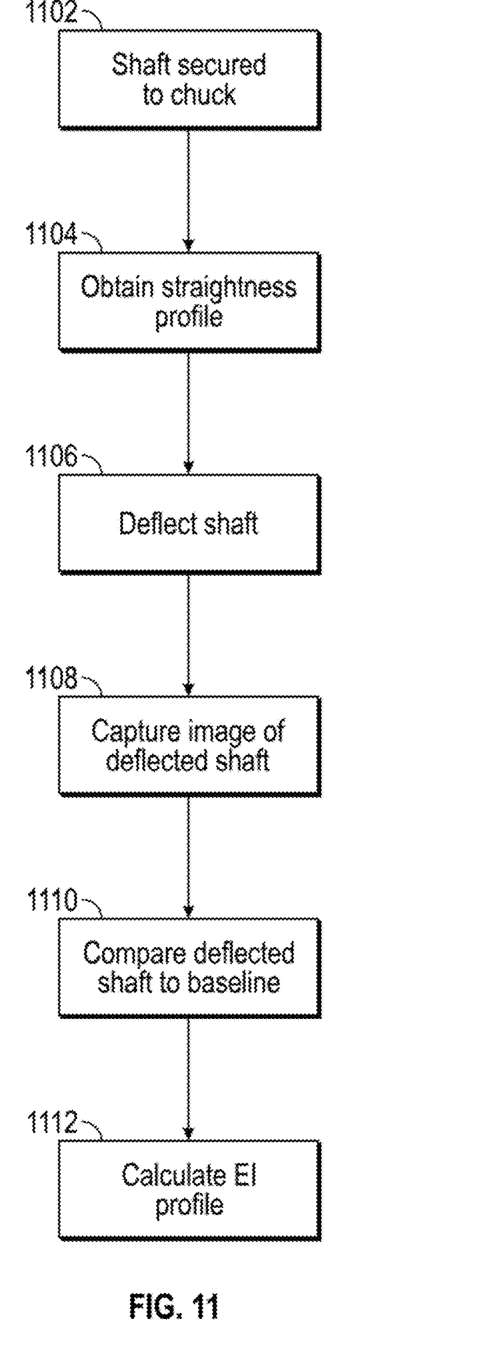
FIG. 11 representatively illustrates a flow chart of a process for measuring a stiffness of a shaft in accordance with an exemplary embodiment of the present technology.

In operation, and referring now to FIGS. 9 and 11, the shaft 104 may be clamped at a first end portion 102 to the chuck 110 (1102). A controller 118 may then direct the chuck 110 and an image capturing system to capture an initial image of the shaft 104 in an unloaded position. A straightness profile for the shaft 104 may then be calculated in the manner described above (1104). Whether or not a straightness profile was calculated, the controller 118 may proceed to direct the loading system 112 to bend the shaft 104 at a second end portion 106 in a cantilevered fashion (1106). The shaft 104 may be bent until a predetermined force is reached or bent until a desired deflection level is reached. While the shaft 104 is bent, the image capturing system may be further instructed to obtain one or more images of the bent shaft 104 (1108). As with the method described above for determining the straightness profile, the bent image of the shaft 104 may be converted into a bitmap format to allow the edges of the shaft 104 to be more easily identified against the background.

Using image analysis, the deflection (or 'bend') profile of the shaft 104 may be measured by a data acquisition system 902 in reference to the deflection datum established by the straightness line from a straightness calibration obtained by the calibration rod or the straightness profile of the shaft 104 (1110). For example, each x-location value may be converted from a pixel location value to a meter value originating from the point where the shaft 104 is inserted the chuck 110 using pre-determined calibration factors. Corresponding to each x-location value, upper and lower edge measurements may be taken for the bent shaft (an excerpt of data values is shown in Table 2 below). A polynomial equation may be fit to each of the top and bottom edge data to generate fitted top and bottom pixel values for each x-location value. The fitted top and bottom edge values may be averaged and the corresponding y-location values from the straightness calibration may be subtracted to obtain an average deflection for each point along the shaft 104. This average deflection may be converted from pixels to meters of deflection using pre-determined calibration factors. Another polynomial equation may be fit to the average deflection data, resulting in the creation of several polynomial coefficients. The resulting coefficients may be saved, exported, or otherwise collected for reproducing the calculated deflection profile for the shaft 104.

TABLE 2

| X Value (pixel) | Top Edge Y Value (pixel) | Bottom Edge Y Value (pixel) | Avg Y Value (pixel) | X Value (meters) | Top Edge Y Fitted Value (pixel) | Bottom Edge Y Fitted Value (pixel) | Generated Y Values based on the Calibration shaft (pixel) | Average Deflection from Calibration Datum (meters) | M_x (N · m) |
|---|---|---|---|---|---|---|---|---|---|
| 0 | 49 | 116 | 82.5 | 0.05842 | 54.8949 | 110.367 | 81.7352 | −0.000279784 | −13.7521 |
| 1 | 49 | 116 | 82.5 | 0.0587323 | 54.9095 | 110.371 | 81.7289 | −0.000284645 | −13.7479 |
| 2 | 49 | 116 | 82.5 | 0.0590446 | 54.9242 | 110.375 | 81.7226 | −0.000289518 | −13.7437 |
| 3 | 49 | 116 | 82.5 | 0.0593569 | 54.9389 | 110.379 | 81.7163 | −0.000294403 | −13.7396 |
| 4 | 50 | 116 | 83 | 0.0596692 | 54.9537 | 110.383 | 81.7099 | −0.000299299 | −13.7354 |
| 5 | 50 | 116 | 83 | 0.0599816 | 54.9684 | 110.387 | 81.7036 | −0.000304206 | −13.7312 |
| . | . | . | . | . | . | . | . | . | . |
| 1000 | 92 | 135 | 113.5 | 0.370731 | 92.1202 | 135.292 | 75.4208 | −0.0119569 | −9.57904 |
| 1001 | 92 | 135 | 113.5 | 0.371043 | 92.1821 | 135.342 | 75.4145 | −0.0119764 | −9.57486 |
| 1002 | 93 | 135 | 114 | 0.371355 | 92.2441 | 135.395 | 75.4082 | −0.0119958 | −9.57069 |
| 1003 | 93 | 135 | 114 | 0.371668 | 92.3062 | 135.442 | 75.4018 | −0.0120153 | −9.56652 |
| 1004 | 93 | 135 | 114 | 0.37198 | 92.3683 | 135.492 | 75.3955 | −0.0120347 | −9.56234 |
| . | . | . | . | . | . | . | . | . | . |
| 2000 | 180 | 214 | 197 | 0.683041 | 180.643 | 214.128 | 69.1064 | −0.0400629 | −5.40599 |
| 2001 | 180 | 214 | 197 | 0.683353 | 180.758 | 214.236 | 69.1001 | −0.0400998 | −5.40182 |
| 2002 | 180 | 214 | 197 | 0.683666 | 180.873 | 214.345 | 69.0938 | −0.0401366 | −5.39764 |
| 2003 | 180 | 214 | 197 | 0.683978 | 180.988 | 214.453 | 69.0874 | −0.0401735 | −5.39347 |
| . | . | . | . | . | . | . | . | . | . |
| 3000 | 318 | 349 | 333.5 | 0.995352 | 319.273 | 349.38 | 62.792 | −0.084803 | −1.23294 |
| 3001 | 319 | 349 | 334 | 0.995664 | 319.433 | 349.539 | 62.7857 | −0.0848548 | −1.22877 |
| 3002 | 319 | 349 | 334 | 0.995977 | 319.592 | 349.698 | 62.7793 | −0.0849066 | −1.22459 |
| 3003 | 319 | 349 | 334 | 0.996289 | 319.752 | 349.857 | 62.773 | −0.0849584 | −1.22042 |
| 3004 | 319 | 350 | 334.5 | 0.996601 | 319.912 | 350.017 | 62.7667 | −0.0850103 | −1.21625 |

Figure 13:
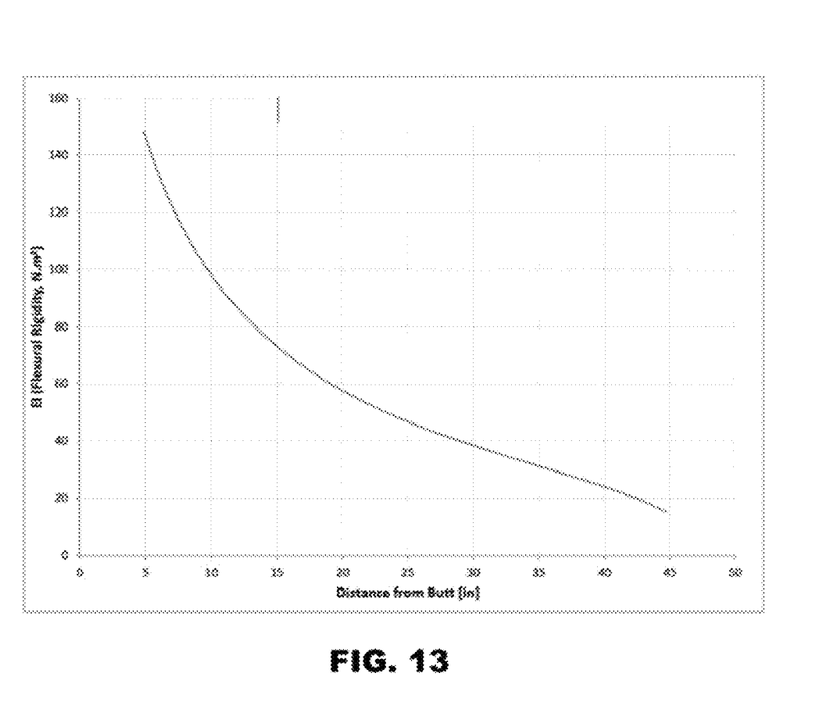
FIG. 13 representatively illustrates a plot of an EI profile in accordance with an exemplary embodiment of the present technology.

Using information relating to the applied load, image data, deflection data, differentiation, and a set of calculations, the EI profile (see FIG. 13) may be calculated by the analysis system for each point, pixel location, or other desired criteria along the length of the shaft 104 (1112). For example, the data acquisition system 902 may then calculate the first and second derivatives of the polynomial equation fit to the average deflection data using any suitable method. The data acquisition system 902 may then obtain the amount of force being applied to the shaft 104 from the load cell and convert it to a moment as a function of the x-location value along the shaft 104 in Newton Meters. For each point along the shaft 104, the EI may be calculated according Equation 1.

Referring again to FIG. 7, the test stand 100 may also be able to measure torsional rigidity ("GJ") profiles of the shaft 104. For example, several lasers 702 may be positioned substantially perpendicularly to and along the length of the shaft 104. The laser 702 position may be tracked optically as they shine on a surface away from the shaft 104. The effective distance of the lasers 702 may be amplified using mirrors to save space while also allowing for greater resolution. The change in position of the lasers before/after a torsion is applied to the shaft 104 will allow an angle of twist at different regions of the shaft 104 to be measured. From this, a GJ or torque profile may be determined.

This test method of measuring GJ may be able to obtain a GJ profile of a shaft 104 for the first time without relying on time consuming and/or expensive destructive methods that currently exist for measuring a GJ profile. This method may also reduce inconsistencies associated with operator-based testing that may occur due to an operator such as reading a gauge using his/her eye. In an alternative embodiment, measuring GJ could be done by using other methods of amplifying the angle of twist of the member such as long protrusions and an optical or infrared tracking system.

The test stand 100 may also be configured to comprise a shaft dampening module that may measure a shaft's dampening ratio/properties. The shaft dampening module may comprise a suitable clamp system and a sensor configured to communicate with the controller. The shaft dampening ratio is essentially a measure of how much energy is lost/conserved when a shaft deflects and returns straight. A shaft with a lower dampening ratio is more efficient when 'springing' back from deflection and will therefore transfer more energy to the ball than a shaft with a higher dampening ratio. Dampening coefficient relates to the percentage of energy lost per cycle during an object's vibration. For this reason, it can be used to describe an object's vibrational energy efficiency.

For example, in operation the sensor may be mounted on the second end portion 106 of the shaft 104 with the first end portion 102 of the shaft 104 securely clamped in the chuck 110. Limiting movement of the clamp and/or sensor during testing may be important to prevent undesired decreases in the calculated dampening due to energy loss in the clamp itself. Any suitable force may be used to place the shaft 104 into oscillation such as by causing a displacement of the second end portion 106 with the loading system. The amount of displacement applied to the second end portion 106 may comprise any suitable value and may be dependent upon the length and/or type of shaft 104 is being tested. The controller may then be activated to measure the oscillation, collect the requisite data, and then determine the shaft dampening ratio.

Although there are instances of energy efficiency/dampening being measured in golf shafts, these methods usually measure the energy efficiency/dampening coefficient by measuring the exponential decay of acceleration data on a single axis. However, this process requires that the golf shaft's vibrations remain in-plane, which is often not the case. By using a logarithmic decrement method and measuring the total energy in the system using the angular velocity about each plane, the shaft dampening module may account for out-of-plane vibrations in the dampening coefficient's calculation over numerous cycles of data. Conversely, techniques that do not account for out-of-plane vibrations will measure lower-than-actual dampening coefficients since energy that moves from in-plane vibrations to out-of-plane vibrations will be perceived as energy loss in the system.

Where KE is the kinetic energy of the system at a certain time (taken once initially after the shaft is put into vibration, and a second reading taken after N cycles of vibration) and is proportional to the sum of the angular velocities, ω, in each of the standard planes of motion:

$$KE \propto \omega_x^2 + \omega_y^2 + \omega_z^2$$

The logarithmic decrement can then be calculated using the equation below:

$$\delta = \frac{KE_1 - KE_N}{N_{KE} \times KE_1}$$

Where $N_{KE}$ is the number of cycles in the kinetic energy data (also equal to the number of peaks in the total kinetic energy data −1). Finally, the logarithmic decrement can be easily used to calculate the dampening ratio, ζ, using:

$$\zeta = \frac{\delta}{\sqrt{4\pi^2 + \delta^2}}$$

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

In the foregoing specification, the invention has been described with reference to specific exemplary embodiments. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described.

For example, the steps recited in any method or process claims may be executed in any order and are not limited to the specific order presented in the claims. Additionally, the components and/or elements recited in any apparatus claims may be assembled or otherwise operationally configured in a variety of permutations and are accordingly not limited to the specific configuration recited in the claims.

Benefits, other advantages and solutions to problems have been described above with regard to particular embodiments; however, any benefit, advantage, solution to problem or any element that may cause any particular benefit, advantage or solution to occur or to become more pronounced are not to be construed as critical, required or essential features or components of any or all the claims.

As used herein, the terms "comprise", "comprises", "comprising", "having", "including", "includes" or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The invention claimed is:

1. A test stand for measuring the physical properties of a member, comprising:
   a chuck configured to selectively receive and secure a first end portion of the member such that a second end portion of the member is cantilevered away from the chuck;
   a load system configured to apply a predetermined load at a predetermined position along the member to cause a deflection along a length of the member between the first and second end portions, wherein the load system comprises an end effector configured to:
      be selectively coupled to between about one-quarter of an inch and five inches of the second end portion of the member to prevent the second end portion of the member from being directly deflected under the effects of the predetermined load; and
      simulate a static end load on the second end portion;
   an image capture system, comprising:
      a light bay having a first end disposed adjacent to the chuck and extending along the length of the member to the second end portion of the member, wherein the light bay is configured to present a lighted background to the member to highlight a contrast between edges of the member and a surrounding environment when the member is secured by the chuck; and
      an image capture device positioned substantially perpendicular from the light bay such that the member is disposed between the light bay and the image capture system when the member is secured by the chuck, wherein the image capture system is configured to:
         capture a first image of the member prior to the application of the predetermined load on the member; and
         capture a second image of the member after the application of the predetermined load on the member;
   a data acquisition system communicatively linked to the image capture system, the load system, and the chuck, wherein the data acquisition system is configured to compare the second image against the first image to calculate at least one of a stiffness profile and a straightness score for the member.

2. A test stand according to claim 1, wherein the load system comprises a load cell configured to apply the predetermined load to the member.

3. A test stand according to claim 2, wherein:
   the chuck is configured to apply a torque to the member;
   the load cell:
      is configured to couple to the second end portion to prevent a rotation of the member at the second end portion; and further comprises a torque sensor configured to measure a torque applied to the member by the chuck; and the data acquisition system is configured to calculate a torque profile for the member.

4. A test stand according to claim 2, wherein the load cell further comprises:
 a first drive screw configured to move the load cell along the length of the member; and
 a load platform configured to move the load cell perpendicular to the chuck.

5. A test stand according to claim 2, wherein the end effector is configured to engage the load cell, wherein the predetermined load is applied to the end effector substantially perpendicular to a longitudinal axis extending through the member.

6. A test stand according to claim 1, wherein the predetermined load comprises a force of between about one pound and about thirty pounds.

7. A test stand according to claim 1, wherein the predetermined load comprises a deflection of the second end portion of between about two inches and about twelve inches.

8. A test stand according to claim 1, wherein the image capture system further comprises a plurality of lasers configured to identify and track at least one of a rotational movement and a deflection of the member.

9. A test stand according to claim 8, wherein the image capture system may be configured to identify any change in movement of the lasers in response to a torsional force applied to the member.

10. A test stand according to claim 1, wherein the data acquisition system comprises:
 a user interface; and
 a controller responsive to the user interface and configured to control the load cell and the chuck.

11. A test stand according to claim 1, wherein:
 the chuck is further configured to rotate the member about a longitudinal axis in at least two increments of between three degrees and 180 degrees of rotation;
 the image capture system is configured to capture an image of the member along its entire length at each increment; and
 the data acquisition system is further configured to calculate a straightness score for the member.

12. A test stand according to claim 1, further comprising a dampening module configured to measure oscillation of the member following an application of an oscillating force to the second end portion.

13. A test stand for measuring the physical properties of a shaft, comprising:
 a chuck configured to receive and secure a first end portion of the shaft such that a second end portion of the shaft is cantilevered outward from the chuck;
 a light bay, comprising:
  a first end disposed adjacent to the chuck;
  a second end disposed outward from the chuck, wherein the light bay is configured to present a lighted background to the shaft to increase a contrast between the shaft and the lighted background when the shaft is secured by the chuck;
 a load cell positioned proximate the second end of the light bay, wherein the load cell is configured to:
  move along the length of the shaft;
  move perpendicular to the chuck; and
  apply a load to the shaft;
 an image capture system positioned away from the light bay such that the shaft is disposed between the light bay and the image capture system when the shaft is secured by the chuck; and
 a data acquisition system communicatively linked to the image capture system, the load cell, and the chuck.

14. A test stand according to claim 13, further comprising an end effector configured to:
 be coupled to between about one-quarter of an inch and five inches of the second end portion of the shaft to prevent the second end portion of the shaft from being directly deflected under the effects of the predetermined load;
 simulate a static end load on the second end portion; and
 engage the load cell.

15. A test stand according to claim 13, wherein the load cell is configured to apply a load to the shaft substantially perpendicular to a longitudinal axis originating at the first end portion of the shaft.

16. A test stand according to claim 13, wherein the image capture system is configured to capture image data of the shaft resulting from an application of the applied load from the load cell on the shaft.

17. A test stand according to claim 13, wherein the data acquisition system comprises:
 a user interface;
 a controller responsive to the user interface and configured to control the load cell and the chuck; and
 a data analysis system responsive to the controller and the image capture system, wherein the data analysis system is configured to calculate at least one of a deflection, stiffness, torque profile, and dampening properties of the shaft.

18. A test stand according to claim 17, wherein:
 the chuck is configured to rotate the shaft about a longitudinal axis in at least two increments of between one degree and 180 degrees of rotation;
 the image capture system is configured to capture an image of the shaft along its entire length at each increment; and
 the data analysis system is configured to calculate a straightness profile of the shaft.

19. A method of determining a straightness score and stiffness profile for a shaft comprising:
 inserting a first end portion of the shaft into a receiving section of a chuck;
 securing the first end portion with the chuck;
 creating a baseline profile of the shaft with an image capture system and a data acquisition system, wherein:
  the image capture system captures a first image of the shaft; and
  the data acquisition system identifies from the first image a top edge and a lower edge of the shaft at multiple points along the length of the shaft;
 creating a straightness profile for the shaft with the image capture system and the data acquisition system, wherein:
  the data acquisition system:
   compares the top edge and the lower edge of the shaft at each point along the length of the shaft to calculate an average value at each point;
   generates a polynomial equation according a plotted data set based on the calculated average to calculate a revised average vertical position for each point along the length of the shaft; and
   compares the calculated revised average vertical position for each point along the length of the shaft against a corresponding point of a calibration rod to generate the straightness profile;

applying a load to a second end portion of the shaft with a load system to cause a deflection of the shaft;

creating a deflection profile of the shaft with the image capture system and the data acquisition system, wherein:

the image capture system captures a second image of the shaft; and the data acquisition system identifies from the second image a top edge and a lower edge of the shaft at multiple points along the length of the shaft;

comparing the baseline profile to the deflection profile to calculate a stiffness profile for the shaft.

20. A method of determining a straightness score and stiffness profile for a shaft according to claim 19, wherein creating a straightness profile score comprises:

rotating the shaft about a longitudinal axis with the chuck in at least two increments of between one degree and 180 degrees of rotation;

capturing an image of the shaft along its entire length at each increment with the image capture system; and calculating a straightness score of the shaft with the data analysis system by comparing a straightness value of the shaft for each increment.

21. A method of determining a straightness score and stiffness profile for a shaft according to claim 19, wherein:

creating a baseline profile of the shaft comprises capturing an image of a reference object along its entire length with the image capture system;

creating a deflection profile of the shaft comprises capturing an image of the shaft along its entire length with the image capture system after the application of the load; and calculating a stiffness profile comprises comparing the deflection profile against the baseline profile with a data acquisition system.

* * * * *